(12) United States Patent
Trauzzi

(10) Patent No.: US 11,118,163 B2
(45) Date of Patent: Sep. 14, 2021

(54) SEPARATION OF CELL POPULATIONS BY MARKER IDENTIFICATION AND SEDIMENTATION VELOCITY

(71) Applicant: Sartorius Stedim Biotech GmbH, Göttingen (DE)

(72) Inventor: Erika Trauzzi, Bayside, NY (US)

( * ) Notice: Subject to any disclaimer, the term of this patent is extended or adjusted under 35 U.S.C. 154(b) by 893 days.

(21) Appl. No.: 15/423,362

(22) Filed: Feb. 2, 2017

(65) Prior Publication Data

US 2020/0048607 A1 Feb. 13, 2020

(51) Int. Cl.
| | | |
|---|---|---|
| *C12N 5/0783* | (2010.01) | |
| *C12N 5/078* | (2010.01) | |
| *C12N 11/04* | (2006.01) | |
| *C12N 5/00* | (2006.01) | |
| *C12M 1/26* | (2006.01) | |

(52) U.S. Cl.
CPC ......... *C12N 5/0638* (2013.01); *C12N 5/0081* (2013.01); *C12N 5/0634* (2013.01); *C12N 11/04* (2013.01); *C12M 33/10* (2013.01); *C12N 2539/00* (2013.01)

(58) Field of Classification Search
None
See application file for complete search history.

(56) References Cited

U.S. PATENT DOCUMENTS 9,790,467 B2 * 10/2017 Kevlahan ........... C07K 16/2809

FOREIGN PATENT DOCUMENTS

| EP | 2636501 A1 | 9/2011 |
|---|---|---|
| WO | 2012106658 A1 | 8/2012 |
| WO | 2017153974 | 9/2017 |
| WO | 2017161371 | 9/2017 |

OTHER PUBLICATIONS

Smith et al., Abstract LB19 from 23rd Annual ISCT Meeting, "Industrializing the Hospital—A fully closed, automated method for processing hematopoietic stem cell transplants", p. e11. May 2-3, 2017 (Year: 2017).*

Armstead, A., et al., "Enhanced Enrichment and Purification of Blood-Derived T-Cells Using a Novel Hydrogel Technology", Blood Journal, Jan. 1, 2015, vol. 126(23), p. 5437. [Retrieved from the Internet Nov. 8, 2017: <URL:http://www.bloodjournal.org/content/126/23/5437?sso-checked=true>] (Abstract only).

Brindley, D.A., et al., "Automation of CAR-T Cell Adoptive Immunotherapy Bioprocessing: Technology Opportunities to Debottleneck Manufacturing", BioProcess International, Apr. 18, 2016. [Retrieved from the Internet Nov. 8, 2017:<URL:http://www.bioprocessintl.com/manufacturing/cell-therapies/automation-of-car-t-cell-adoptive-immunotherapy-bioprocessing-technology-opportunities-to-debottleneck-manufacturing/>].

Hatch, A., et al., "Engineered Alginate Hydrogels for Effective Microfluidic Capture and Release of Endothelial Progenitor Cells from Whole Blood", Langmuir, Apr. 5, 2011, vol. 27(7), pp. 4257-4264, doi:10.1021/la105016a.

Hatch, A., et al., "Tag-Free Microfluidic Separation of Cells Against Multiple Markers", Analytical Chemistry, May 2, 2012, vol. 84(10), pp. 4618-4621, doi:10.1021/ac300496q.

Jesuraj, N.J., et al., "A Novel Phase-Change Hydrogel Substrate for T Cell Activation Promotes Increased Expansion of CD8+ Cells Expressing Central Memory and Naive Phenotype Markers", Blood, Dec. 2, 2016, vol. 128(22), p. 3368 (Abstract only).

Shah, A.M., et al., "Biopolymer System for Cell Recovery from Microfluidic Cell Capture Devices", Analytical Chemistry, Mar. 10, 2012, vol. 84(8), pp. 3682-3688, doi:10.1021/ac300190j.

Smith, D., et al., "LB18 The Future of T-Cell Therapy—Fully Closed and Automated Manufacturing Using Novel Capture LB19 Industrializing the Hospital—A Fully Closed, Automated Method tor Processing Hematopoietic Stem Cell Transplants", 23rd Annual ISCT Meeting E11. [Retrieved from the Internet Nov. 9, 2017:<URL:https://ac.els-cdn.com/S146532491730453X/1-s2.0-S146532491730453X-main.pdf?_tid=b84a28c2-c559-11 e7-8eeb-00000aab0f26&acdnat=1510237659_b9f21ccf7b389f2cdfc9ec28e5ca682e>] (Abstract only).

Tran, C-A., et al., "Optimized Processing of Growth Factor Mobilized Peripheral Blood CD34+ Products by Counterflow Centrifugal Elutriation", Stem Cells Translational Medicine, May 1, 2012, vol. 1(5), pp. 422-429, doi: 10.5966/sctm.2011-0062.

International Search Report and Written Opinion, from the International Searching Authority of the European Patent Office, for International Application No. PCT/EP2017/001072, dated Dec. 1, 2017, pp. 1-15.

* cited by examiner

*Primary Examiner* — Allison M Fox

(57) ABSTRACT

The present invention relates to methods for the specific separation of target cells from a biological sample, comprising specific binding of the target cells to phase-change hydrogel compositions and separation of respective cell-hydrogel complexes by counter-current centrifugation.

12 Claims, 1 Drawing Sheet

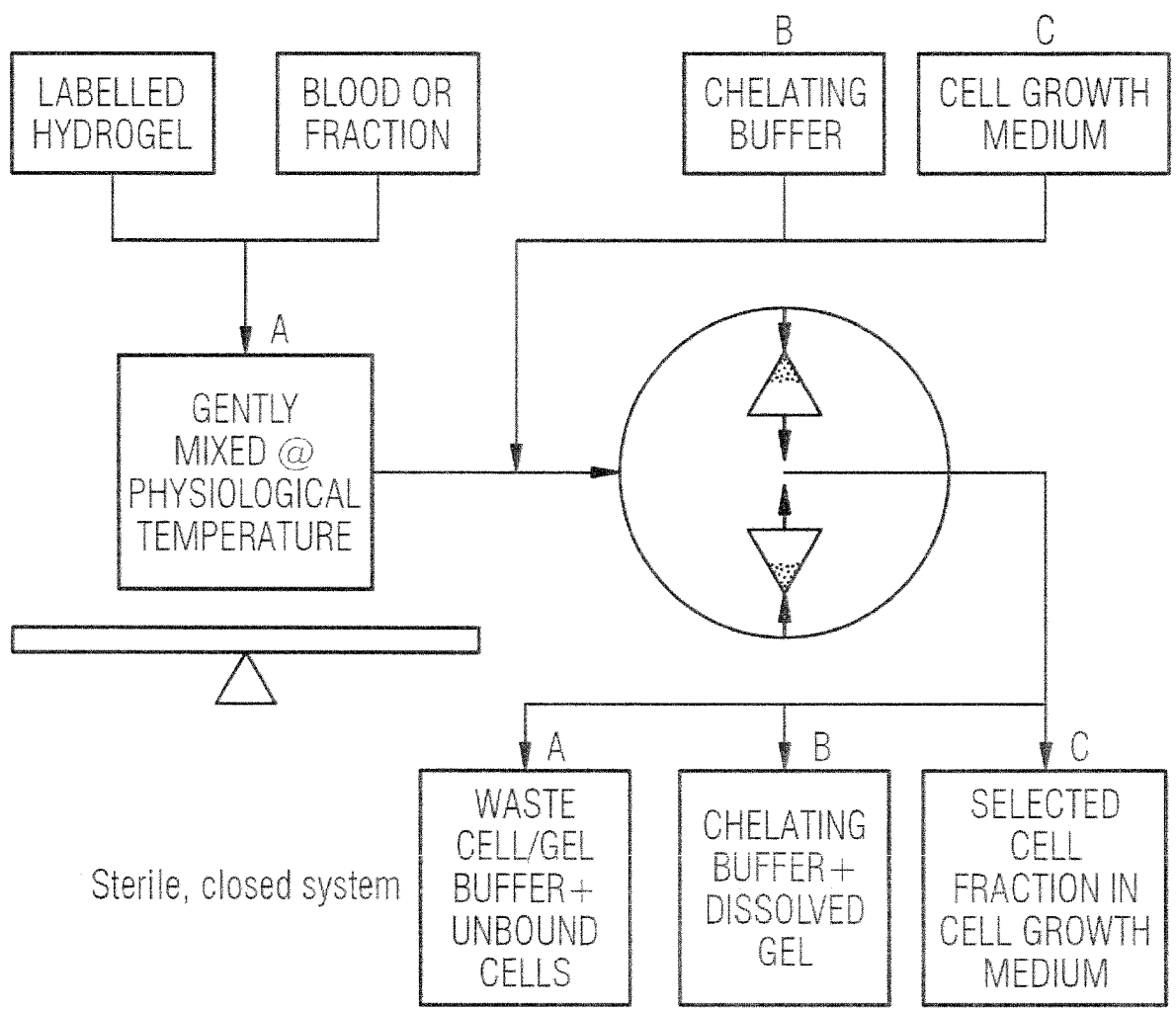

SEPARATION OF CELL POPULATIONS BY MARKER IDENTIFICATION AND SEDIMENTATION VELOCITY

FIELD OF THE INVENTION

The present invention relates to methods for the specific separation of target cells from a biological sample, comprising specific binding of the target cells to phase-change hydrogel compositions and separation of respective cell-hydrogel complexes by counter-current centrifugation.

BACKGROUND OF THE INVENTION

The isolation and purification of cells out of complex biological samples based on predefined cell characteristics nowadays is widely employed in laboratories all over the world. The ability to do so has led to significant advances in basic and applied biological, physiological and medical research.

Of particular interest in this respect is the separation of cells for use in immunotherapies such as e.g. adoptive T cell transfer. Currently, cells produced for immunotherapies are separated by their cell surface markers using magnetic separation techniques such as e.g. the Miltenyi MACS® and/or Thermo Fisher Dynabeads® systems.

However, magnetic separation techniques take a significant amount of time, upwards of two hours, and then require the dilution of the magnetic particles out of culture prior to administering the cells to a patient: In this context, the FDA requires a level of less than 100 magnetic particles per ml. This can take four to five days of culturing to dilute the magnetic particles out. Further, the use of magnetic particles can be detrimental to cell viability, e.g. resulting from shear forces occurring during magnetic separation.

Therefore, a strong need exists to provide methods for the specific separation of target cells from a biological samples, said methods allowing for a fast separation of unlabeled cells while maintaining cell viability, as well as for a direct use of said cells in applications such as immunotherapies.

This need is satisfied by providing the embodiments characterized in the claims.

DESCRIPTION OF THE DRAWINGS

FIG. 1 shows an exemplary workflow diagram of a method according to the present invention.

SUMMARY OF THE INVENTION

The present invention describes methods for the highly specific separation of unlabeled viable cells out of complex biological samples. These methods employ the specific binding of target cells to phase-change hydrogel compositions, i.e., hydrogel compositions that can reversibly exist in polymerized and depolymerized states depending on outside conditions. Further, said methods employ counter-current centrifugation for the actual separation of target cell-hydrogel complexes. Respective methods can advantageously be used in the production of cell-based therapeutics such as T cell-based immunotherapeutics, but are ultimately useful in all applications requiring the separation of viable cells by their cell surface markers.

In particular, the present invention relates to methods for the specific separation of target cells from a biological sample, comprising the steps of providing a phase-change hydrogel composition, the hydrogel being labeled with biological moieties that are capable of specifically interacting with the target cells; incubating the biological sample with said hydrogel composition under conditions allowing polymerization of the hydrogel and binding of the target cells to the hydrogel via said biological moieties, thus forming cell-hydrogel complexes; separating said cell-hydrogel complexes from unbound cells and other components of the biological sample in a centrifugation vessel by sedimentation velocity in a counter-current centrifuge; depolymerizing the hydrogel once the cell-hydrogel complexes are separated by applying suitable conditions within the centrifugation vessel in the counter-current centrifuge; removing the depolymerized hydrogel composition from the centrifugation vessel in the counter-current centrifuge; and transferring the separated target cells into a collection vessel.

DETAILED DESCRIPTION OF THE INVENTION

The present invention relates to a method for the specific separation of target cells from a biological sample, comprising the steps of:

(a) providing a phase-change hydrogel composition, the hydrogel being labeled with biological moieties that are capable of specifically interacting with one or more marker(s) on the target cells;

(b) incubating the biological sample with said hydrogel composition under conditions allowing polymerization of the hydrogel and binding of the target cells to the hydrogel via said biological moieties, thus forming cell-hydrogel complexes;

(c) separating said cell-hydrogel complexes from unbound cells and other components of the biological sample in a centrifugation vessel via their sedimentation velocity in a counter-current centrifuge;

(d) depolymerizing the hydrogel once the cell-hydrogel complexes are separated by applying suitable conditions within the centrifugation vessel in the counter-current centrifuge;

(e) removing the depolymerized hydrogel composition from the centrifugation vessel in the counter-current centrifuge; and (f) transferring the separated target cells into a collection vessel.

As used herein, the term "specific separation" indicates that separation occurs in a directed and targeted manner, i.e., in a manner that aims at separating all target cells and only the target cells.

The term "target cells" as used herein relates to any population of cells of interest. This may be a homogeneous population, a heterogeneous population or a mixed cell population. Accordingly, the biological moieties that are capable of specifically interacting with the target cells, with which the hydrogel is labeled, can be homogeneous, i.e., provide specific interaction with a single marker on the target cells, or can be heterogeneous, i.e., provide specific interaction with multiple markers on one or more types of target cells. Thus, in a preferred embodiment, the hydrogel is labeled with multiple biological moieties that are capable of specifically interacting with multiple markers on one type of target cells or on multiple types of target cells.

In preferred embodiments, the biological moieties that are capable of specifically interacting with one or more marker(s) on the target cells are capable of specifically binding to said one or more marker(s). More preferably, the biological moieties are selected from the group consisting of antibodies, antibody fragments, and antibody mimetics. Preferably, antibody fragments are selected from the group consisting of Fab fragment, Fab' fragments, F(ab')$_2$ fragments, and single-chain variable fragments (scFv). Further, antibody mimetics are preferably selected from the group consisting of single domain antibodies, small modular immunopharmaceuticals (SMIPs), affibodies, affilins, affimers, affitins, aptamers, alphabodies, anticalins, avimers, DARPins, and monobodies.

In other preferred embodiments, the biological moieties that are capable of specifically interacting with one or more marker(s) on the target cells, and the respective markers on the target cells, are generic biologically relevant binding pairs known in the art, e.g. Ni$^{2+}$-containing moieties such as Ni-NTA as biological moiety on the hydrogel and a His-tag as marker on the target cells, or biotin and streptavidin as marker on the target cells and biological moiety on the hydrogel or vice versa.

In preferred embodiments, the target cells are immune cells, more preferably T cells of any T cell lineage, NK cells, tumor infiltrating cells (TILs), or immune cells having target cell-killing activity, and most preferably cytotoxic T cells. In a particular example, the cells are chimeric antigen receptor (CAR)-T cells as known in the art.

The biological samples to be used in the methods of the present invention are not particularly limited and include any aqueous solution or medium containing or suspected of containing target cells. In preferred embodiments, the biological samples is selected from whole blood, cell culture samples, and blood fractions such as apharesis fractions or peripheral blood mononuclear cells (PBMCs).

In step (a) of the method of the present invention, a phase-change hydrogel composition is provided, the hydrogel being labeled with biological moieties that are capable of specifically interacting with one or more marker(s) on the target cells. Phase-change hydrogels are hydrogels that can be reversibly polymerized and depolymerized by applying suitable conditions, e.g. buffer conditions. Respective phase-change hydrogels are not particularly limited and are known in the art.

Conditions for allowing polymerization of a phase-change hydrogel or for keeping said hydrogel in a polymerized state include conditions wherein depending on the mechanism of polymerization of the hydrogel, specific temperatures are applied, or certain ions or molecules that interact chemically with the hydrogel to create the polymerization effect are added or removed. The same applies in an analogous manner to conditions for allowing depolymerization of a phase-change hydrogel or for keeping said hydrogel in a depolymerized state. Respective conditions are known in the art for any given type of phase-change hydrogel.

In certain embodiments, the phase-change hydrogel is polymerized around a further substrate, selected from the group consisting of metal particles, magnetic particles, non-phase-change polymers, glass particles. In particular embodiments, the further substrate may be a material that triggers the phase-change of the hydrogel.

Methods for labeling a phase-change hydrogel with biological moieties that are capable of specifically interacting with one or more marker(s) on the target cells are not particularly limited and are known in the art.

In step (b) of the method of the present invention, the biological sample is incubated with said hydrogel composition under conditions allowing polymerization of the hydrogel and binding of the target cells to the hydrogel via said biological moieties, thus forming cell-hydrogel complexes. In this context, the term "conditions allowing polymerization of the hydrogel" is not intended to imply that the hydrogel composition cannot be in a polymerized form prior to the incubation. In particular, said term is expressly intended to include the possibility of keeping the hydrogel in an already polymerized state. Further, conditions allowing for the binding of the target cells to the hydrogel via said biological moieties are not particularly limited and are known in the art. Such conditions include a suitable duration of the incubation.

In step (c) of the method of the present invention, the cell-hydrogel complexes formed in step (b) are separated from unbound cells and other components of the biological sample in a centrifugation vessel via their sedimentation velocity in a counter-current centrifuge.

Counter-current centrifuges are devices for separating cells via so-called counterflow centrifugation elutriation (CCE). The basic principle of separating cells via CCE is the balance between centrifugal forces and opposing counter flow drag forces of a flowing buffer solution. When cells enter the elutriation chamber, cells will stay at the outer edge of the chamber due to centrifugal forces. Then, with increasing flow rate of the buffer solution, cells are pushed towards the center of the chamber. As the flow rate of the buffer solution increases further, when the counter flow drag forces outweigh the centrifugal forces, smaller cells will be driven by the net force and leave the chamber first. In contrast, larger cells will stay within the elutriation chamber. Respective methods and counter-current centrifuge for use in the context of the present invention are not particularly limited and are known in the art. They include for example counter-current centrifuges available from Sartorius Stedim Biotech, Bohemia, N.Y., USA under the name kSep® Systems.

As used herein, the term "via their sedimentation velocity" indicates that the initial separation of cell-hydrogel complexes from unbound cells and other components of the biological sample occurs within the counter-current centrifuge and according to the principles of CCE based on differences in the respective sedimentation velocities.

In step (d) of the method of the present invention, the hydrogel is depolymerized once the cell-hydrogel complexes are separated by applying suitable conditions within the centrifugation vessel in the counter-current centrifuge. Respective conditions are as defined above. Of note, the depolymerization is effected and occurs within the centrifugation vessel in the counter-current centrifuge, e.g. by applying a suitable buffer as defined above.

Once the depolymerization of the hydrogel has occurred, the depolymerized hydrogel composition is removed from the centrifugation vessel in the counter-current centrifuge in step (e) of the method of the present invention, e.g. by applying a suitable counterflow.

Finally, in step (f) of the method of the present invention, the separated target cells are transferred into a collection vessel.

In preferred embodiments, the method of the present invention is performed in a sterile environment and/or does not require any manual manipulation steps.

Preferably, the methods of the present invention are in vitro methods, i.e., they are methods that are not practiced on the human or animal body.

As indicated above, the present invention describes methods for the highly specific separation of unlabeled viable cells out of complex biological samples. Said methods can advantageously be used in the production of cell-based therapeutics such as T cell-based immunotherapeutics, but are ultimately useful in all applications requiring the separation of viable cells by their cell surface markers.

The methods of the present invention advantageously can be performed in a low shear environment, thus maintaining cell viability. Further, said methods are much faster than conventional column or magnet based separation techniques, removing several days from the production process of e.g. cell-based immunotherapeutics. Furthermore, said methods do not require the exposure of the target cells to magnetic particles or other agents that may have negative impacts on cell viability and which would have to be removed prior to administering the cells to a patient. Moreover, said methods avoid the co-separation of dead cells. Finally, said methods can be easily performed in a sterile environment and do not require any manual manipulation steps.

The FIGURE shows:

FIG. 1 shows an exemplary workflow diagram of a method according to the present invention.

The present invention will be further illustrated by the following example without any limitation thereto.

EXAMPLE

PBMCs were mixed with a polymerized hydrogel that has been modified with anti-CD4 antibodies, in a sterile bag. The bag was incubated at 37° C. for 0.5 hours and then connected to a single-use centrifuge, which transferred the cell/hydrogel mix into the single-use chamber of the centrifuge as it was rotating. The cell/hydrogel mix formed a loose pellet or fluidized bed inside the centrifuge chamber, and a sterile buffer was washed through to remove impurities, including dead or unbound cells, as they had a different sedimentation velocity compared to the bound cells.

After washing, the conditions to enact a phase change of the hydrogel were applied (e.g. a temperature shift or change in buffer composition). The hydrogel depolymerized and was washed through, while cells remained sedimented or in a fluidized bed. The appropriate formulation buffer was washed through and the direction of flow reversed to eject the desired cells into a new sterile chamber. Fluid flow paths were managed by manual or automated activation of a single-used compatible valve system.

The invention claimed is:

1. A method for the specific separation of target cells from a biological sample, the method comprising the steps of:
   (a) providing a phase-change hydrogel composition and providing magnetic particles, the hydrogel composition being labeled with biological moieties that are capable of specifically interacting with one or more marker(s) on the target cells;
   (b) incubating the biological sample with said hydrogel composition and said magnetic particles under conditions allowing for simultaneous polymerization of the hydrogel composition around said magnetic particles and binding of the target cells to the hydrogel composition via said biological moieties, thus forming cell-hydrogel complexes;
   (c) separating said cell-hydrogel complexes from unbound cells and other components of the biological sample in a centrifugation vessel via their sedimentation velocity in a counter-current centrifuge;
   (d) depolymerizing the hydrogel composition once the cell-hydrogel complexes are separated by applying suitable conditions within the centrifugation vessel in the counter-current centrifuge;
   (e) separating the target cells and removing the depolymerized hydrogel composition from the centrifugation vessel in the counter-current centrifuge; and
   (f) transferring the separated target cells into a collection vessel.

2. The method of claim 1, wherein the target cells are immune cells.

3. The method of claim 2, wherein said immune cells are selected from the group consisting of T cells, NK cells, tumor infiltrating cells (TILs), and immune cells having target cell-killing activity.

4. The method of claim 3, wherein the T-cells are cytotoxic T cells.

5. The method of claim 1, wherein the target cells are chimeric antigen receptor (CAR)-T cells.

6. The method of claim 1, wherein the biological sample is selected from the group consisting of whole blood, blood fractions, apheresis fractions, peripheral blood mononuclear cells (PBMCs), and cell culture samples.

7. The method of claim 1, wherein the hydrogel composition is labeled with multiple biological moieties that are capable of specifically interacting with multiple markers on one type of target cells or on multiple types of target cells.

8. The method of claim 1, wherein the biological moieties that are capable of specifically interacting with one or more marker(s) on the target cells are capable of specifically binding to said one or more marker(s).

9. The method of claim 8, wherein the biological moieties are selected from the group consisting of antibodies, antibody fragments, and antibody mimetics.

10. The method of claim 9, wherein the antibody fragments are selected from the group consisting of Fab fragment, Fab' fragments, F(ab')$_2$ fragments, and single-chain variable fragments (scFv).

11. The method of claim 9, wherein the antibody mimetics are selected from the group consisting of single domain antibodies, small modular immunopharmaceuticals (SMIPs), affibodies, affilins, affimers, affitins, aptamers, alphabodies, anticalins, avimers, DARPins, and monobodies.

12. The method of claim 1, wherein the method is performed in a sterile environment.

* * * * *